United States Patent [19]

Shawl et al.

[11] Patent Number: 4,873,364

[45] Date of Patent: Oct. 10, 1989

[54] PROCESS FOR THE PREPARATION OF METHYLENE DIPHENYLENE DIISOCYANATES AND POLYMETHYLENE POLYPHENYLENE POLY (DIISOCYANATES)

[75] Inventors: Edward T. Shawl, Wallingford; Haven S. Kesling, Jr., Drexel Hill, both of Pa.

[73] Assignee: Arco Chemical Technology, Inc., Wilmington, Del.

[21] Appl. No.: 283,430

[22] Filed: Dec. 9, 1988

[51] Int. Cl.⁴ .......................................... C07C 118/00
[52] U.S. Cl. .................................................. 560/344
[58] Field of Search ........................................ 560/344

[56] References Cited

U.S. PATENT DOCUMENTS 2,773,086 12/1956 Slocombe et al. .
3,898,259 8/1975 Hearsey .
3,936,484 2/1976 Rosenthal et al. .
4,223,145 9/1980 Hentschel et al. .................. 560/344
4,223,145 9/1980 Hentschel et al. .

FOREIGN PATENT DOCUMENTS 1473821 2/1967 France .
1359032 7/1974 United Kingdom ................ 560/344

OTHER PUBLICATIONS

Hofmann, Proc. Royal Soc., London, 9, 274 (1858).
Bennet et al., J. Am. Chem. Soc., 75, 2101 (1952).

*Primary Examiner*—Alan Siegel
*Attorney, Agent, or Firm*—Delbert E. McCaslin

[57] ABSTRACT

An improved process is provided for the preparation of methylene diphenylene diisocyanates (MDI) and polymethylene polyphenylene poly (diisocyanates) by the thermal decomposition of a methylene diphenylene bis (dialkylurea) or a polymethylene polyphenylene poly (dialkylurea) in a solvent in the presence of a tertiary amine hydrohalide, such as pyridine hydrochloride, as a promoter for conversion of the urea groups to the corresponding isocyanate.

12 Claims, No Drawings

PROCESS FOR THE PREPARATION OF METHYLENE DIPHENYLENE DIISOCYANATES AND POLYMETHYLENE POLYPHENYLENE POLY (DIISOCYANATES)

FIELD OF THE INVENTION

The present invention relates to an improved process for the preparation of methylene diphenylene diisocyanates and the higher polymethylene polyphenylene poly (diisocyanate) homologs thereof (commonly known in the trade as MDI and PMDI respectively) by heating in an inert solvent a methylene diphenylene bis (dialkyl urea) or a polymethylene polyphenylene poly (dialky urea) in the presence of a tertiary amine hydrohalide, such as pyridine hydrochloride, as a promoter to convert the urea groups to isocyanate groups and recovering the respective isocyanates from the reaction mixtures.

BACKGROUND OF THE INVENTION

A number of processes have been reported for the preparation of various diisocyanates and polysiocyanates by the vapor or solvent phase decomposition of substituted ureas.

The production of aromatic isocyanates from symmetrical bis aryl ureas in the presence of hydrogen chloride, phosphorus pentoxide or zinc chloride was described by A. Hofmann in the Proc. Royal Soc., London, Vol. IX, p. 274 (1858). By heating a mixture of diphenyl urea with phosphorus pentoxide, zinc chloride or gaseous HCl, Hofmann distilled phenyl isocyanate overhead. No details of the experimental procedure are presented and the yield of isocyanate is not given.

A. Hofmann, Chemisch Berichte, Vol. 3, pp. 653–658 (1870) described heating diphenyl urea in the presence of phosphoric acid giving yields too small to be considered for the preparation of the isocyanate.

Subsequent work by Iwakura and Nagakubo reported in the Bulletin Tokyo Inst. Technol., Vol. 13, p. 25 (1950) and Chemical Abstracts, Vol. 44, p. 3924E (1950) describes the preparation of an aromatic isocyanate (p-ethoxyphenylisocyanate) by heating a solution of bis aryl urea such as bis (p-ethoxyphenyl) urea in the presence of hydrogen chloride gas.

The vapor phase decomposition of bis aryl ureas at 350° C. and higher temperatures has been described by W. d. Bennet et al, Journ. Am. Chem. Soc., Vol. 75, p. 2101 (1952) and Slocombe et al in U.S. Pat. No. 2,773,086, Dec. 4, 1956 in the presence of gaseous HCl as a promoter. Yields are reported in the 60 to 70% range for the vapor phase reaction and only a 5% yield for liquid phase reaction. A carbamoyl chloride intermediate is formed.

The liquid phase decomposition of trisubstituted ureas to isocyanates has been described by van Landeghem et al, French Pat. No. 1,473,521, Feb. 13, 1967; C. H. Hearsey, U.S. Pat. No. 3,898,259, Aug. 5, 1975 and Rosenthal et al in the U.S. Pat. No. 3,936,484, Feb. 3, 1976. van Landeghem shows thermal decomposition of trisubstituted ureas in an organic solvent having specified dielectric constants at 140° to 170° C. with long reaction times of from 6 to 10 hours and modest yields of 60 to 70%. A variety of catalysts are shown but not exemplified or claimed, and include metal salts, such as acetates, stearates, and linoleates of manganese, zinc, cobalt, chromium and vanadium, tertiary amine bases, such as aliphatic, cycloaliphatic, aromatic and mixed tertiary amines, aliphatic heterocyclic amines such as N-methylpiperidine or N, N'-dimethylpiperidine as well as aromatic heterocyclic amines such as pyridine and pyrimidine. Other nitrogen compounds such as imidazole are indicated as being suitable. However, under the reaction conditions described tertiary amines as shown by van Landeghem do not catalyze urea decomposition.

Rosenthal et al U.S. Pat. No. 3,936,484 discloses the thermal decomposition of di- and tri-substituted ureas to isocyanates at temperatures above 230° C. in a solvent and isocyanate yields of from 60 to 80%.

The Hearsey U.S. Pat. No. 3,898,259 describes the introduction of gaseous hydrogen chloride into the liquid phase urea decomposition reaction to give reduced reaction times with isocyanate yields of from 80–90%. An excess of gaseous HCl is employed and a by-product carbamoyl chloride intermediate formed.

A. Hentschel et al U.S. Pat. No. 4,223,145, Sept. 16, 1980 discloses the formation of an HCl adduct of a trisubsubstituted urea using at most a 10% excess of HCl. This adduct is then decomposed in a closed system at from 80°–180° C.

Applicants have found that hydrohalide salts of tertiary amines are very effective promoters for the thermal decomposition of methylene diphenylene bis (dialkyl ureas) and polymethylene polyphenylene poly (dialkyl ureas) to the corresponding iscoyanate at relatively mild reaction temperatures and short residence times in an organic solvent. Although it has been shown that the hydrohalide acids (HCl) promote urea decomposition, it is unexpected that the salts of these acids, especially, tertiary amine salts of these acids would be effective promoters.

SUMMARY OF THE INVENTION

This invention reltes to a novel improved process for the preparation of methylene diphenylene diisocyanates (MDI) and polymethylene polyphenylene poly (diisocyanates) (PDMI) from a methylene diphenylene bis (dialky urea) or polymethylene polyphenylene poly (dialkyl urea) which comprises thermally treating the respective urea which has been dissolved in or slurried with an inert organic solvent in the presence of a hydrohalide salt of a tertiary amine to produce the corresponding isocyanate. The MDI or PMDI produced by the instant invention are of significant industrial importance and are particularly useful as intermediates in producing products for agricultural application and in the preparation of polyurethenaes.

It is an object of the present invention therefore, to provide an improved process for the production of MDI and PMDI from the corresponding urea in high yield and high conversion of the urea.

It is another object of this invention to provide an improved reaction (thermal decomposition) system for the conversion of the bis (dialkyl ureas) and the poly (dialkyl ureas) to the corresponding isocyanates.

These and other objects and advantages of this invention will become apparent from the description of the invention which follows and the claims.

DETAILED DESCRIPTION OF THE INVENTION

In accordance with the present invention, methylene diphenylene diisocyanates or polymethylene polyphenylene poly (diisocyanates) are produced by heating at temperatures of from about 50° C. to about 220° C.

preferably from about 90° C. to 150° C., a methylene diphenylene bis (dialkylurea) having the general formula

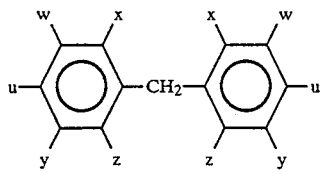

or the higher polymethylene polyphenylene poly (dialkylurea) homologs thereof having the structural formula

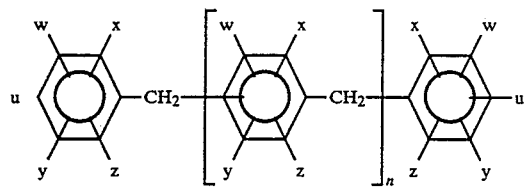

wherein at least one of the substituents u, w, x, y and z on the ring is a dialkylureido (—NHCONRR') group and the other substituents which may be different on the ring, are hydrogen, an ether group or a nitro group, R and R' which may be the same or different are an alkyl group having independently from 1 to 8 carbon atoms and n is an integer of from 1 to 8 dissolved or slurried in an organic solvent or mixture of solvents, which are stable and substantially chemically inert to the components of the reaction system, in the presence of a tertiary amine hydrohalide, such as pyridine hydrochloride or bromide, to convert the urea groups to isocyanate groups and the desired methylene diphenylene diisocyanate or polymethylene polyphenylene poly (diisocyanate) product separated and recovered.

The R' and R" of the dialkylureido (—NHCONRR') group set forth hereinabove may be substituted or unsubstituted mono-, di-, or trivalent radicals selected from saturated or mono-olefinic unsaturated straight or branched chain aliphatic or cycloaliphatic radicals optionally containing alkoxyalkyl radicals with one or more ether linkages, aryl radicals, or aralkyl radicals. These radicals may be substituted with groups which are non-reactive with the isocyanates produced by the process of the invention, such as, for example, nitro or halo groups. Also included are cycloaliphatic and substituted cycloaliphatic radicals containing from 5 to 7 carbon atoms such as cyclopentyl, cyclohexyl and cycloheptyl radicals.

Representative methylene diphenylene bis (dialkylureas) which may be employed in the process of the present invention include, for example, methylene diphenylene bis (dimethylurea), methylene diphenylene bis (diethylurea), methylene diphenylene bis (dibutylurea) and the like as well as the polymethylene polyphenylene ply (dimethylurea), polymethylene polyphenylene poly (diethyl or dibutyl or dipropyl ureas) and the like. These urea compounds are merely representative of a large number of ureas falling within the above described formulae which can be converted to diisocyanates in the solvent phase in the presence of a tertiary amine hydrohalide promoter.

The tertiary amine hydrohalide salts employed in the process of the present invention to promote thermal decomposition of the dialkyl ureas to the corresponding diisocyanate may be prepared, for example by reacting the tertiary amine selected with a hydrogen halide such as HCl. Salts of hydrogen fluoride, chloride, bromide or iodide may be used. The tertiary amines used to prepare the hydrohalide will conform to the general formula R,R',R"N wherein R,R' and R" are not hydrogen but may be an apliphatic radical having from 1 to 10 carbon atoms, a cycloaliphatic radical such as cyclophentyl, cyclohexyl and cycloheptyl radicals, an aromatic radical, or an aralkyl radical. Such radicals may be substituted with, for example, nitro or halo groups which are non-reactive with the isocyanate produced. Suitable amine salts include, for example, triethylamine hydrochloride, hydrobromide or hydrofluoride, trioctylamibe hydrochloride, hydrobromide or hydrofluoride, N-methyldiethylamine hydrobromide or hydrochloride, N,N-di ethylaniline hydrochloride and N,N-dimethylcyclohexylamine hydrochloride. Hydrohalide salts of heterocyclic tertiary amines and heterocyclic aromatic amines may also be employed. Representative satls include, for example, N-methylpyrrolidine hydrochloride, pyridine hydrochloride or hydrobromide, 3-ethylpyridine hydrochloride, the hydrohalide salt of 1,4-diazabicyclo [2.2.2]octane, 4-chloropyridine hydrochloride, 4,4'-bipyridine dihydrochloride, quinoline hydrochloride or hydrobromide and the like. Salts of amine oxides such as 2-chloropyridine N-oxide hydrochloride may also be used as a promoter. In addition, the hydrohalide may be formed with an amine which may be part of the polymer such as polyvinyl pyridine or a resin prepared from tertiary amine groups attached to a styrene divinylbenzene polymer. The tertiary amine hydrohalide is generally employed in the process at a molar ratio of one to one based on the urea groups. Howwever, an excess of the tertiary amine hydrohalide promoter may be used.

The process of the present invention can be suitably carried out by adding the bis (dialkyl urea) or poly (dialkyl urea) to a solvent or a mixture of solvents comprising the reaction medium. The urea may be soluble in the solvent or solvents or soluble at reaction temperature or the urea may be in the form of a slurry. Suitable solvents which may be employed include, for example, the aromatic hydrocarbons such as benzene, toluene, xylene, trimethylbenzene, tetrahydronapthalene as well as the higher alkyl-substituted aromatic hydrocarbons; alkanes and substituted alkanes as well as cyaloalkanes having from 5 to 20 carbon atoms, such as, for example, n-hexane, n-heptane, octane, nonane, cyclohexane, dodecane, octadecane, 2-methylhexane, 2-ethylhexane, methylcyclohexane, and the like; halogenated or nitrated aromatic and aliphatic hydrocarbons such as, for example, methylene chloride, carbon tetrachloride, 1,2-dichloroethane, tetrachloroethane, chlorobenzenes, nitrobenzenes, dinitrotoluene and the like; aromatic or aliphatic ethers such as, for example diphenylether; dibutylether, porpyleneglycol dimethyl ether, and the like; tertiary amines, such as, for example, pyridine, treithylamine N-methylpyrrolidone and the like.

The process of the present invention may be carried out as a batch, semi-continuous or continuous process and the order of addition of the materials and reactants may be varied to suit the particular apparatus employed. For example, in a batch process all the urea, the solvent and the tertiary amine hydrohalide may be charged together to the reaction vessel and then heated to reaction temperature, or, the tertiary amine hydrohalide and some solvent may be added to the reactor, heated to the desired reaction temperature, and then the urea or the urea and additional solvent added to the mixture; the urea may be totally dissolved in the additional solvent or it may be added as a slurry in the solvent. The added materials can be maintained at any convenient temperature. In addition, the urea and solvent can be added to the reactor and then the tertiary amine hydrohalide added over a period of time by means of a solids addition apparatus. Depending of the choice of solvent and tertiary amine hydrohalide employed, the reaction product may be a single phase or it may have an organic phase and a salt phase. If the reaction product has two phases, the organic phase can be decanted from the salt phase. If the tertiry amine is higher boiling than the secondary amine by-product formed during reaction of the urea, then the secondary amine can be recovered by fractional distillation and reused in synthesis of the urea. The tertiary amine salt may be regenerated and reused as a promoter for urea decomposition.

The reaction of the invention may be carried out in any suitable reactor which is equipped with a means for temperature control and agitation. Heating and/or cooling means may be employed interior or exterior of the reaction vessel to maintain temperature within the desired range.

As indicated hereinabovee, the thermal decomposition of the bis (dialkyl ureas) or poly (dialkyl ureas) is carried out at temperatures of from about 50° C. to about 220° C., preferably from about 90° C. to 150° C. Reaction time is dependent on decomposition temperature but will generally range between about 5 minutes and several hours. The reaction is generally carried out at atmospheric pressure, but depending on the boiling points of the solvents employed and the isocyanate product, it may be carried out at super-atmospheric or sub-atmospheric pressures. The diisocyanates formed may be recovered by filtration, by distillation, or by other known methods, depending on the solvent, tertiary amine salt employed and the diisocyanate produced.

The present invention is more fully illustrated by the following examples, which include particular features of the invention. However, the examples are not to be construed as limiting the invention in any way, it being understood that numerous variations are possible without departing from the spirit and scope of the invention.

EXAMPLE 1

A mixture of 3.95 g, 10.0 mmoles, of 4,4'-methylene diphenylene bis (diethylurea), and 2.90 g, 25.1 mmoles, of pyridine hydrochloride in 100 g of o-xylene was added to a 250 ml round bottom flask fitted with a magnetic stirrer, condenser, and a thermocouple for measuring reaction temperature. The mixture was heated to reflux at 142° C. for 60 min. A sample was taken from the pot and analyzed by infrared spectroscopy for the NCO group. Another sample was taken from the xylene phase and reacted with ethanol to convert isocyanate groups to ethyl carbamate groups. This product was then analyzed by high pressure liquid chromatography (HPLC). Conversion of the starting bis (diethyl urea) was 98% with a selectivity of 93% to 4,4'-methylene diphenylene diisocyanate and 5% to the monodiethylurea derivative.

EXAMPLE 2

The procedure of Example 1 was repeated using 3.50 g of a poly methylene polyphenylene poly (diethylurea), 4.20 g pyridine hydrobromide and 100 g toluene. The mixture was heated at 110° C. for 120 min. Analysis by infrared spectroscopy and HPLC showed 85% conversion of urea groups to isocyanates.

EXAMPLE 3

A mixture of 20 g 4,4'-methylene diphenylene bis (dimethylurea) and 14 g pyridine hydrochloride in 500 g o-xylene was heated for 90 min at 140° C. in a 1000 ml round bottom flask equipped with a mechanical stirrer and condenser. At the end of the reaction, the organic phase was decanted from the salt phase and the salt phase was extracted with hot o-xylene. Analysis of the combined organic product and extract showed 98% conversion of the urea and 95% selectivity to methylene diphenylene diisocyanate. The diisocyanate was recovered from the organic phase by fractional distillation under reduced pressure.

EXAMPLE 4

A mixture of 15 g methylene diphenylene bis (diethylurea) and 10 g pyridine hydrochloride in 100 g mesitylene was heated to reflux at 161° C. for 120 min in a 250 ml flask equipped with a mechanical stirrer and condenser. Conversion of the bis (diethylurea) was 99% with selectivity of 98% to methylene diphenylene diisocyanate.

EXAMPLE 5-12

A number of runs were made in accordance with the procedure of Example 1, utilizing various bis (dialkylurea) or poly (dialkylurea) compounds, tertiary amine hydrohalide salts, solvents and conditions. Reaction materials, conditions and analytical results are set forth in the table below.

TABLE

| | | EXAMPLES 5-12 | | | | | |
|---|---|---|---|---|---|---|---|
| Ex. No. | Urea (g)* | Amine* Salt (g) | Solvent (g) | Temp. (°C.) | Time (Min) | Conversion of Urea (%) | Isocyanate Selectivity |
| 5 | MUMDI (3.4) | Qu.HCl (3.1) | O—dichlorobenzene (100) | 180 | 90 | 85 | 95 |
| 6 | MUMDI (6.8) | Bipy. HCl (5.1) | O—xylene (100) | 142 | 60 | 50 | 80 |
| 7 | BUMDI (5.1) | Py.HBr (3.5) | O—xylene (100) | 142 | 90 | 96 | 97 |
| 8 | EUPMDI (3.9) | Py.HCl (2.4) | diphenylether (100) | 150 | 60 | 90 | 90 |
| 9 | MUMDI (3.4) | NEM.HCl (1.8) | mesitylene (100) | 160 | 30 | 70 | 85 |
| 10 | EUMDI (3.9) | 2ClpyN—O (3.6) | hexadecane (100) | 140 | 120 | 75 | 90 |

TABLE-continued
EXAMPLES 5-12

| Ex. No. | Urea (g)* | Amine* Salt (g) | Solvent (g) | Temp. (°C.) | Time (Min) | Conversion of Urea (%) | Isocyanate Selectivity |
|---------|-----------|-----------------|-------------|-------------|------------|------------------------|------------------------|
| 11 | EUMDI (3.4) | py.HCl (2.9) | tetrachloro-ethane (100) | 130 | 60 | 95 | 95 |
| 12 | EUPMDI (3.9) | 4Clpy.HCl (3.2) | dichlorohenzene (100) | 180 | 60 | 94 | 96 |

MUMDI = methylene diphenylene bis (dimethylurea)
EUMDI = methylene diphenylene bis (diethylurea)
BUMDI = methylene diphenylene bis (di-n-butyurea)
EUPMDI = polymethylene polybenzlene poly (diethylurea)
4Cl py.HCl = 4-chloropyridine hydrochloride
2Cl pyN—O = 2-chloropyridine-N—oxide hydrochloride
Py.HCl = pyridine hydrochloride
py.HBr = pyridine hydrobromide
Qu—HCl = Quinuclidine hydrochloride
NEM.HCl = N—ethylomorpholine hydrochloride
Bipy.HCl = 4,4'-dipyridyl dihydrochloride

We claim:

1. A process for the preparation of a methylene diphenylene diisocyanate or a polymethylene polyphenylene poly (diisocyanate) which comprises heating at a temperature within the range of from about 50° C. to about 220° C. a methylene diphenylene bis (dialkylurea) having the formula

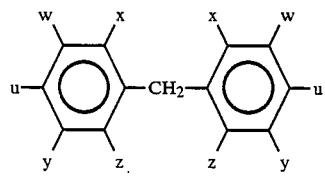

or a polymethylene polyphenylene poly (dialkylurea) having the formula

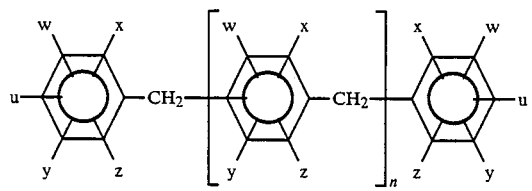

wherein at least one of the substituents u, w, x, y and z on the ring is a dialkylureido (—NHCONRR') group and the other substituents which may be the same or different on the ring, are hydrogen, an ether group or a nitro group, R and R' of the dialkylureido group which may be the same or different are an alkyl group having indepedently from 1 to 8 carbon atoms and n is an integer of from 1 to 8, dissolved or slurried in an organic solvent or mixture of solvents, in the presence of a tertiary amine hydrohalide as a promoter to convert the urea to the corresponding diisocyanate, and thereafter separating and recovering the diiscoayanate or poly (diisocyanate).

2. A process according to claim 1 wherein the temperature is in the range of from 90° C. to 150° C.

3. A process according to claim 1 wherein the methylene diphenylene bis (dialkylurea) is selected from the group consisting of methylene diphenylene bis (dimethylurea), methylene diphenylene bis (diethylurea) and methylene diphenyl bis (di-n-butylurea).

4. A process according to claim 1 wherein the polymethylene polyphenylene poly (dialkylurea) is polymethylene polyphenylene poly (diethylurea).

5. A process according to claim 1 wherein the tertiary amine hydrohalide is selected from the group consisting of pyridine hydrochloride, pyridine hydrobromide, 4-chloropyridine hydrochloride, 2-chloropyridine-N-oxide hydrochloride, Quinuclidine hydrochloride, N-ethylmorpholine hydrochloride and 4,4'-dipyridyl dihydrochloride.

6. A process according to claim 5 wherein the tertiary amine hydrohalide is pyridine hydrochloride.

7. A process according to claim 1 wherein the organic solvent is selected from the group consisting of toluene, o-xylene, mesitylene, diphenylether, o-dichlorobenzene, tetrachloroethane and hexadecane.

8. A process according to claim 7 wherein the solvent is o-xylene.

9. A process according to claim 7 wherein the solvent is toluene.

10. A process for the preparation of a methylene diphenylene diisocyanate which comprises heating at a temperature of from about 90° C. to about 150° C. a methylene diphenyl bis (dialkylurea) having the formula

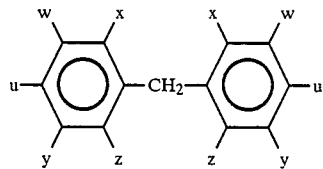

wherein at least one of the substituents, u, w, x, y and z on the ring is a dialkylureido (—NHCONRR') group and the other substituents which may be the same or different on the ring are hydrogen, an ether group or a nitro group and R and R' of the dialklureido group are an alkyl group having independently from 1 to 8 carbon atoms, dissolved in or slurried in an organic solvent or mixture of solvents in the presence of a tertiary amine hydrohalide as a promoter to convert the urea to the isocyanate and thereafter separating and recovering the isocyanate.

11. A process according to claim 10 wherein the methylene diphenylene bis (dialkylurea) is methylene dephenylene bis (diethylurea).

12. A process according to claim 10 wherein the tertiary amine hydrohalide is pyridine hydrochloride.

* * * * *